(12) United States Patent  
Mault

(10) Patent No.: US 6,478,736 B1  
(45) Date of Patent: Nov. 12, 2002

(54) INTEGRATED CALORIE MANAGEMENT SYSTEM

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 12 days.

(21) Appl. No.: 09/685,625

(22) Filed: Oct. 10, 2000

Related U.S. Application Data

(60) Provisional application No. 60/158,553, filed on Oct. 8, 1999, provisional application No. 60/167,276, filed on Nov. 24, 1999, provisional application No. 60/177,016, filed on Jan. 19, 2000, provisional application No. 60/177,011, filed on Jan. 19, 2000, provisional application No. 60/178,979, filed on Jan. 28, 2000, provisional application No. 60/194,126, filed on Apr. 3, 2000, provisional application No. 60/200,428, filed on Apr. 28, 2000, provisional application No. 60/207,051, filed on May 25, 2000, provisional application No. 60/207,089, filed on May 25, 2000, provisional application No. 60/209,921, filed on Jun. 7, 2000, provisional application No. 60/219,069, filed on Jul. 18, 2000, provisional application No. 60/219,512, filed on Jul. 20, 2000, and provisional application No. 60/228,680, filed on Aug. 29, 2000.

(51) Int. Cl.$^7$ .......................... A61B 5/00; A61B 5/083; G06F 17/00

(52) U.S. Cl. ...................... 600/300; 128/921; 600/531; 708/131

(58) Field of Search .............................. 600/300, 301, 600/531, 532, 538; 128/897–925; 708/131, 133

(56) References Cited

U.S. PATENT DOCUMENTS

| | | | |
|---|---|---|---|
| 2,630,798 A | 3/1953 | White et al. | 128/2.07 |
| 2,826,912 A | 3/1958 | Kritz | 73/194 |
| 2,831,348 A | 4/1958 | Kritz | 73/861.28 |

(List continued on next page.)

FOREIGN PATENT DOCUMENTS

| | | |
|---|---|---|
| DE | 198 10 476 | 9/1998 |
| EP | 0459647 | 10/1991 |
| EP | 0 712 638 | 12/1995 |
| GB | 2323292 | 9/1998 |
| WO | WO 96/40340 | 12/1996 |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise."

British Journal Of Anaesthesia, vol. 49, 1977 London (GB) pp. 575–587, J. A. Bushman et al. "Closed Circuit Anaesthesia.".

IEEE Transactions on Biomedical Engineering, vol. 35, No. 9, Sep. 1988, pp. 653–659, Capek et al., "Noninvasive Measurement of Cardia Output Using Partial CO2 ReBreathing."

Clinics in Chest Medicine (Review), vol. 10, 1989, pp. 255–264, Heigenhauser et al., "Measurement if Cardiac Output by Carbon Dioxide Rebreathing Methods."

Determination Of Nitric Oxide Levels by Fluorescence Spectroscopy, Gabor G. and Allon N. in Biochemical, Pharmacological, and Clinical Aspects of Nitric Oxide, edited by B. A. Weissman et al., Plenum Press, New York, 1995, p. 57.

*Primary Examiner*—Eric F. Winakur  
*Assistant Examiner*—David McCrosky  
(74) *Attorney, Agent, or Firm*—Gifford, Krass, Groh, Sprinkle, Anderson & Citkowski, P.C.

(57) ABSTRACT

An improved health management system for a person is disclosed, in which the person's resting metabolic rate (RMR) is determined at intervals using an indirect calorimeter. RMR values are used in setting and revising goals in, for example, a weight control program. The effects of a weight control program on RMR can hence be compensated for, which enables an improved weight control program to be developed. In one embodiment, the person is provided with a portable electronic device, for use as a caloric intake calculator, caloric expenditure calculator, and caloric balance calculator.

49 Claims, 11 Drawing Sheets

U.S. PATENT DOCUMENTS

| | | | | |
|---|---|---|---|---|
| 2,838,399 | A | 6/1958 | Vogel, Jr. | 99/48 |
| 2,869,357 | A | 11/1959 | Kritz | 73/32 |
| 2,911,825 | A | 11/1959 | Kritz | 73/194 |
| 2,920,012 | A | 1/1960 | Sanders et al. | 167/51.5 |
| 3,213,684 | A | 10/1965 | Seaton et al. | 73/190 |
| 3,220,255 | A | 11/1965 | Scranton et al. | 73/204 |
| 3,250,270 | A | 5/1966 | Bloom | 128/2.07 |
| 3,306,283 | A | 2/1967 | Arp | 128/2.07 |
| 3,523,529 | A | 8/1970 | Kissen | 128/2.07 |
| 3,527,205 | A | 9/1970 | Jones | 128/2.08 |
| 3,681,197 | A | 8/1972 | Smith | 195/63 |
| 3,726,270 | A | 4/1973 | Griffis et al. | 128/2.08 |
| 3,799,149 | A | 3/1974 | Rummel et al. | 128/2.07 |
| 3,814,091 | A | 6/1974 | Henkin | 128/188 |
| 3,834,375 | A | 9/1974 | Sanctuary et al. | 128/2.07 |
| 3,895,630 | A | 7/1975 | Bachman | 128/2.07 |
| 3,938,551 | A | 2/1976 | Henkin | 137/613 |
| 3,962,917 | A | 6/1976 | Terada | 73/204 |
| 3,979,480 | A | 9/1976 | Radici et al. | 525/425 |
| 3,991,304 | A | 11/1976 | Hillsman | 235/151.34 |
| 4,003,396 | A | 1/1977 | Fleischmann | 137/83 |
| 4,031,847 | A | 10/1977 | Henkin | 128/145.6 |
| 4,078,554 | A | 3/1978 | Lemaitre et al. | 128/2.08 |
| 4,095,274 | A | 6/1978 | Gordon | 364/715 |
| 4,100,401 | A | 7/1978 | Tutt et al. | 235/92 T |
| 4,101,071 | A | 7/1978 | Brejnik et al. | 235/92 MT |
| 4,151,668 | A | 5/1979 | Hungerford | 40/495 |
| 4,159,416 | A | 6/1979 | Brejnik et al. | 235/92 MT |
| 4,186,735 | A | 2/1980 | Henneman et al. | 128/201.25 |
| 4,188,946 | A | 2/1980 | Watson et al. | 128/204.22 |
| 4,192,000 | A | 3/1980 | Lipsey | 364/415 |
| 4,197,857 | A | 4/1980 | Osborn | 600/531 |
| 4,200,094 | A | 4/1980 | Gedeon et al. | 128/201.13 |
| 4,211,239 | A | 7/1980 | Raemer et al. | 128/716 |
| 4,221,079 | A | 9/1980 | Segar et al. | 364/900 |
| 4,221,224 | A | 9/1980 | Clark | 128/718 |
| 4,221,959 | A | 9/1980 | Sessler | 377/13 |
| 4,230,108 | A | 10/1980 | Young | |
| 4,244,020 | A | 1/1981 | Ratcliff | 364/413 |
| 4,321,674 | A | 3/1982 | Krames et al. | 364/413 |
| 4,341,867 | A | 7/1982 | Johansen | 435/189 |
| 4,359,057 | A | 11/1982 | Manzella | 128/713 |
| 4,368,740 | A | 1/1983 | Binder | 128/718 |
| 4,380,802 | A | 4/1983 | Segar et al. | 364/900 |
| 4,386,604 | A | 6/1983 | Hershey | 128/718 |
| 4,387,777 | A | 6/1983 | Ash | 177/43 |
| 4,425,805 | A | 1/1984 | Ogura et al. | 73/861.29 |
| 4,440,177 | A | 4/1984 | Anderson et al. | 600/532 |
| 4,444,201 | A | 4/1984 | Itoh | 128/716 |
| 4,463,764 | A | 8/1984 | Anderson et al. | 600/532 |
| 4,566,461 | A | 1/1986 | Lubell et al. | 128/668 |
| 4,571,682 | A | 2/1986 | Silverman et al. | 364/413 |
| 4,572,208 | A | 2/1986 | Cutler et al. | 128/718 |
| 4,575,804 | A | 3/1986 | Ratcliff | 364/715 |
| 4,598,700 | A | 7/1986 | Tamm | 128/671 |
| 4,608,995 | A | 9/1986 | Linnarsson et al. | 128/713 |
| 4,619,269 | A | 10/1986 | Cutler et al. | 128/719 |
| 4,629,015 | A | 12/1986 | Fried et al. | 177/25 |
| 4,648,396 | A | 3/1987 | Raemer | 600/534 |
| 4,650,218 | A | 3/1987 | Hawke | 283/67 |
| 4,658,832 | A | 4/1987 | Brugnoli | 600/532 |
| 4,686,624 | A | 8/1987 | Blum et al. | 364/415 |
| 4,709,331 | A | 11/1987 | Barkett et al. | 364/413 |
| 4,731,726 | A | 3/1988 | Allen, III | 364/416 |
| 4,753,245 | A | 6/1988 | Gedeon | 128/718 |
| 4,756,670 | A | 7/1988 | Arai | 417/43 |
| 4,757,453 | A | 7/1988 | Nasiff | 364/415 |
| 4,781,184 | A | 11/1988 | Fife | 128/205.12 |
| 4,796,182 | A | 1/1989 | Duboff | 364/413.29 |
| 4,796,639 | A | 1/1989 | Snow et al. | 600/532 |
| 4,803,625 | A | 2/1989 | Fu et al. | 364/413.03 |
| 4,807,169 | A | 2/1989 | Overbeck | 364/715.01 |
| 4,823,808 | A | 4/1989 | Clegg et al. | 128/773 |
| 4,850,371 | A | 7/1989 | Broadhurst et al. | 600/532 |
| 4,853,854 | A | 8/1989 | Behar et al. | 364/413.01 |
| 4,855,945 | A | 8/1989 | Sakai | 364/709.02 |
| 4,856,531 | A | 8/1989 | Merilainen | 600/532 |
| 4,891,756 | A | 1/1990 | Williams, III | 364/413.29 |
| 4,894,793 | A | 1/1990 | Ikemoto et al. | 364/709.03 |
| 4,909,259 | A | 3/1990 | Tehrani | 600/531 |
| 4,911,256 | A | 3/1990 | Attikiouzel | 177/25.16 |
| 4,914,959 | A | 4/1990 | Mylvaganam et al. | 73/861.28 |
| 4,917,108 | A | 4/1990 | Mault | 128/718 |
| 4,924,389 | A | 5/1990 | Gerbaulet et al. | 364/413.29 |
| 4,951,197 | A | 8/1990 | Mellinger | 364/413.2 |
| 4,954,954 | A | 9/1990 | Madsen et al. | 364/413.29 |
| 4,955,946 | A | 9/1990 | Mount et al. | 600/532 |
| 4,986,268 | A | 1/1991 | Tehrani | 128/204 |
| 4,998,018 | A | 3/1991 | Kurahashi et al. | 250/343 |
| 5,022,406 | A | 6/1991 | Tomlinson | 128/719 |
| 5,033,561 | A | 7/1991 | Hettinger | 177/25.16 |
| 5,038,773 | A | 8/1991 | Norlien et al. | 128/205.23 |
| 5,038,792 | A | 8/1991 | Mault | 128/718 |
| 5,042,500 | A | 8/1991 | Norlien et al. | 600/532 |
| 5,042,501 | A | 8/1991 | Kenny et al. | 600/532 |
| 5,060,506 | A | 10/1991 | Douglas | 73/24.1 |
| 5,060,655 | A | 10/1991 | Rudolph | 128/716 |
| 5,060,656 | A | 10/1991 | Howard | 128/718 |
| 5,069,220 | A | 12/1991 | Casparie et al. | 128/719 |
| 5,072,737 | A | 12/1991 | Goulding | 128/718 |
| 5,081,871 | A | 1/1992 | Glaser | 73/863.23 |
| 5,095,900 | A | 3/1992 | Fertig et al. | 128/207.14 |
| 5,095,913 | A | 3/1992 | Yelderman et al. | 128/719 |
| 5,117,674 | A | 6/1992 | Howard | 73/31.07 |
| 5,119,825 | A | 6/1992 | Huhn | 600/529 |
| 5,178,155 | A | 1/1993 | Mault | 128/718 |
| 5,179,958 | A | 1/1993 | Mault | 128/718 |
| 5,214,966 | A | 6/1993 | Delsing | 73/861.28 |
| 5,233,520 | A | 8/1993 | Kretsch et al. | 364/413.29 |
| 5,233,996 | A | 8/1993 | Coleman et al. | 600/529 |
| 5,263,491 | A | 11/1993 | Thornton | 128/774 |
| 5,282,473 | A | 2/1994 | Braig et al. | 600/532 |
| 5,285,794 | A | 2/1994 | Lynch | 128/719 |
| 5,293,875 | A | 3/1994 | Stone | 128/719 |
| 5,299,579 | A | 4/1994 | Gedeon et al. | 600/532 |
| 5,303,712 | A | 4/1994 | Van Duren | 600/529 |
| 5,309,921 | A | 5/1994 | Kisner et al. | 600/532 |
| 5,326,973 | A | 7/1994 | Eckerbom et al. | 250/343 |
| 5,355,879 | A | 10/1994 | Brain | |
| 5,357,972 | A | 10/1994 | Norlien | 128/725 |
| 5,363,857 | A | 11/1994 | Howard | 600/531 |
| 5,387,164 | A | 2/1995 | Brown, Jr. | 482/9 |
| 5,388,043 | A | 2/1995 | Hettinger | 364/413.29 |
| 5,398,688 | A | 3/1995 | Laniado | 128/660.02 |
| 5,398,695 | A | 3/1995 | Anderson et al. | 600/532 |
| 5,402,796 | A | 4/1995 | Packer et al. | 128/719 |
| 5,412,560 | A | 5/1995 | Dennisson | 364/413.01 |
| 5,412,564 | A | 5/1995 | Ecer | 364/413.29 |
| 5,419,326 | A | 5/1995 | Harnoncourt | 128/660.02 |
| 5,425,374 | A | 6/1995 | Ueda et al. | 600/532 |
| 5,450,193 | A | 9/1995 | Carlsen et al. | 356/301 |
| 5,454,721 | A | 10/1995 | Kuch | 434/127 |
| 5,468,961 | A | 11/1995 | Gradon et al. | 250/345 |
| 5,478,989 | A | 12/1995 | Shepley | 235/375 |
| 5,503,151 | A | 4/1996 | Harnoncourt et al. | 128/660.02 |
| 5,570,697 | A | 11/1996 | Walker et al. | 128/719 |
| 5,632,281 | A | 5/1997 | Rayburn | 128/719 |
| 5,645,071 | A | 7/1997 | Harnoncourt et al. | 128/719 |
| 5,647,370 | A | 7/1997 | Harnoncourt | 128/725 |
| 5,673,691 | A | 10/1997 | Abrams et al. | 128/630 |
| 5,676,132 | A | 10/1997 | Tillotson et al. | 128/204.23 |

| Patent No. | Date | Inventor | Class |
|---|---|---|---|
| 5,691,927 A | 11/1997 | Gump | 364/709.01 |
| 5,704,350 A | 1/1998 | Williams, III | 128/630 |
| 5,705,735 A | 1/1998 | Acorn | 73/23.3 |
| 5,729,479 A | 3/1998 | Golan | 364/709.02 |
| 5,754,288 A | 5/1998 | Yamamoto et al. | 356/301 |
| 5,789,660 A | 8/1998 | Kofoed et al. | 73/232 |
| 5,796,009 A | 8/1998 | Delsing | 73/861.28 |
| 5,800,360 A | 9/1998 | Kisner et al. | 600/532 |
| 5,810,722 A | 9/1998 | Heikkila | 600/300 |
| 5,816,246 A | 10/1998 | Mirza | 128/726 |
| 5,819,735 A | 10/1998 | Mansfield et al. | 128/630 |
| 5,822,715 A | 10/1998 | Worthington et al. | 702/19 |
| 5,831,175 A | 11/1998 | Fletcher-Haynes | 73/861.28 |
| 5,832,448 A | 11/1998 | Brown | 705/2 |
| 5,834,626 A | 11/1998 | DeCastro et al. | 73/23.3 |
| 5,836,300 A | 11/1998 | Mault | 128/204.23 |
| 5,836,312 A | 11/1998 | Moore | 128/897 |
| 5,839,901 A | 11/1998 | Karkanen | 434/127 |
| 5,890,128 A | 3/1999 | Diaz et al. | 705/2 |
| 5,908,301 A | 6/1999 | Lutz | 434/236 |
| 5,918,603 A | 7/1999 | Brown | 128/897 |
| 5,922,610 A | 7/1999 | Alving et al. | 436/116 |
| 5,932,812 A | 8/1999 | Delsing | 73/861.02 |
| 5,933,136 A | 8/1999 | Brown | 345/327 |
| 5,954,510 A | 9/1999 | Merrill et al. | 434/236 |
| 5,954,640 A | 9/1999 | Szabo | 600/300 |
| 5,957,858 A | 9/1999 | Micheels et al. | 600/532 |
| 5,989,188 A | 11/1999 | Birkhoelzer et al. | 600/300 |
| 6,010,459 A | 1/2000 | Silkoff et al. | 600/532 |
| 6,013,007 A | 1/2000 | Root et al. | 482/8 |
| 6,024,281 A | 2/2000 | Shepley | 235/375 |
| 6,024,699 A | 2/2000 | Surwit et al. | 600/300 |
| 6,030,342 A | 2/2000 | Amano et al. | 600/301 |
| 6,032,119 A | 2/2000 | Brown et al. | 705/2 |
| 6,032,676 A | 3/2000 | Moore | 128/898 |
| 6,039,688 A | 3/2000 | Douglas et al. | 600/300 |
| 6,040,531 A | 3/2000 | Miller-Kovach et al. | 177/25.16 |
| 6,042,383 A | 3/2000 | Herron | 434/238 |
| 6,044,843 A | 4/2000 | O'Neil et al. | 128/204.23 |
| 6,077,193 A | 6/2000 | Buhler et al. | 482/8 |
| 6,083,006 A | 7/2000 | Coffman | 434/127 |
| 6,095,949 A | 8/2000 | Arai | 482/4 |
| 6,095,985 A | 8/2000 | Raymond et al. | 600/513 |
| 6,101,478 A | 8/2000 | Brown | 705/2 |
| 6,135,950 A | 10/2000 | Adams | 600/300 |
| 6,135,951 A | 10/2000 | Richardson et al. | 600/300 |

| Personal Profile | |
|---|---|
| Name: | |
| Birth Date: 9/10/00 Age: 0 | |
| Gender: M F | |
| My goal for my weight is to: | |
| ▼ lose weight/fat | |
| My preferred units: | |
| ▼ US (lb/in) | |

PERSONAL DATA ENTRY

FIG - 7A

| Baseline Measurements | |
|---|---|
| Start Date: 9/10/00 | |
| Height: 0 ft. 0 0 in. | Weight: 0 0 0 lbs. |
| Frame Size: small med large | Select if known otherwise... |
| Body Fat: 1 5 % | Enter if known otherwise... |

STARTING DATA ENTRY

FIG - 7B

BalanceLog Targets
- Body Health
- Weight & Date
- RMR
- Balance
- Nutrition
- Activity Plan

BALANCE LOG TARGETS

FIG - 8A

Balance Target Summary
Calories per Day:
Eat 1549   −1552 Balance   Burn 3101

Resting: 1549
Life-styles: 1352
exercise: 200

At a rate of 1.41 lbs/week, you should reach your goal by 10/1/00

BALANCE TARGET SUMMARY

FIG - 8B

| Nutrient Targets | | |
|---|---|---|
| Calories | 1549 | kcal |
| Total Fat | 34.4 | g |
| Saturated Fat | 10.3 | g |
| Cholesterol | 300 | mg |
| Sodium | 2400 | mg |
| Carbohydrates | 213 | g |
| Dietary Fiber | 312 | g |
| Sugars | 35.1 | g |
| Protein | 96.8 | g |
| Vitamin A | 1000 | RE |
| Vitamin C | 60 | mg |

NUTRIENT TARGETS

FIG - 8C

Exercise Metabolism

Resting
Life-style  } Total Calories
→ Exercise 0 0 0 0 Calories per day burned in exercise ☐ custom or use calculator →
☐ minimum for health
☒ no exercise

ACTIVITY PLAN TARGET

FIG - 8D

RMR TARGETS

FIG - 8E

BODY HEALTH TARGETS

DAILY BALANCE SCREEN

WEEKLY BALANCE SCREEN

BALANCE LOG REPORTS

FUEL MIX
(NUTRITION BREAKDOWN)

BODY TRENDS

INTEGRATED CALORIE MANAGEMENT SYSTEM

REFERENCED TO RELATED APPLICATIONS

This application claims priority from U.S. provisional applications Ser. Nos. 60/158,553, filed Oct. 8, 1999; No. 60/167,276, filed Nov. 24, 1999; No. 60/177,016, filed Jan. 19, 2000; No. 60/177,011, filed Jan. 19, 2000; No. 60/178,979, filed Jan. 28, 2000; No. 60/194,126, filed Apr. 3, 2000; No. 60/200,428, filed Apr. 28, 2000; No. 60/207,051, filed May 25, 2000; No. 60/207,089, filed May 25, 2000; No. 60/209,921, filed Jun. 7, 2000; No. 60/219,069, filed Jul. 18, 2000; No. 60/219,512, filed Jul. 20, 2000; and 60/228,680, filed Aug. 29, 2000, all of which are incorporated herein in their entirety by reference.

FIELD OF THE INVENTION

This invention relates to health management, in particular, to weight control.

BACKGROUND OF THE INVENTION

Good health and weight control are of considerable interest to a large number of people. Many people engage in conventional weight loss schemes, usually based on a restricted calorie diet. Physical activity may be included in a weight control program. A calorie management system allows a person to compare their caloric expenditure, comprising resting metabolic rate (RMR) and activity-related caloric expenditure, to their caloric intake in the form of food and beverages. Caloric expenditure has two components, a larger contribution related to resting metabolic processes, and a smaller contribution related to the energy expended in physical activity. We may say that total energy expenditure (TEE) is the sum of resting energy expenditure (REE, a product of resting metabolic rate and the time-period of interest) and activity related energy expenditure (AEE), i.e.:

$$TEE = REE + AEE$$

Caloric balance is defined in terms of the difference between TEE and the caloric intake of the person.

In some prior systems of weight control, a person's RMR has been estimated using the Harris-Benedict equation, which relates RMR to body height, weight, age, and gender. This equation is well known to those skilled in the diet and nutrition arts (e.g. Williams, certificate of correction to U.S. Pat. No. 5,704,350, and Krause and Mahon, "Food Nutrition and Diet Therapy"). Alternatively, charts and tables, usually based on the Harris-Benedict equation, may be used. Additional demographic factors and body fat percentage may be included to improve the estimate of RMR.

It is important to realize that the values of RMR obtained using equations, tables, charts and the like, only provide an estimated RMR value for an average person. A person with a given height, weight, or other physical parameter (such as may be entered into the Harris-Benedict equation or modified equation) may have an actual RMR that is significantly different from the estimate. Actual RMR values for individuals within a group of apparently similar persons will fall on a distribution around the estimated RMR value for an average person. This distribution leads to errors in the caloric needs calculated for a person in a weight control program.

Additionally, there is an even more serious inadequacy in conventional weight control programs. The RMR of a person changes unpredictably as a weight control program progresses. A person may respond to the perceived starvation conditions through a significant drop in RMR. As a consequence, such a person may even gain weight on a reduced calorie diet if their caloric intake required to maintain a given weight falls below the reduced value prescribed by the diet. This is an unsatisfactory outcome to a weight control program. Other people may suffer no fall in metabolic rate during the restricted calorie diet. If the weight control program contains an exercise component, the resting metabolic rate of a person may even increase during the program. The Harris-Benedict equation predicts that resting metabolism will fall as body weight is lost, but is not intended to predict the actual response of a person's resting metabolic rate to a weight control program. Hence, estimating the resting metabolic rate of a person using an equation may lead to large errors in calculating the caloric needs and activity levels required for an effective weight control program. Hence, an improved weight control method which accurately compensates for changes in metabolic rate over time will be of great value.

RMR can be determined using an indirect calorimeter. Conventional devices are large, expensive, and difficult to use so that expert assistance is essential. A person will need to report to a specific location, such as a hospital, for use of a conventional indirect calorimeter. There is considerable difficulty and expense associated with conventional indirect calorimeter use, so that conventional weight loss programs do not monitor the RMR of the person in the program, but rather rely on an estimate such as provided by the Harris Benedict equation.

A very large number of weight loss approaches have been proposed, all of which suffer from the above discussed shortcomings. For example, in U.S. Pat. No. 5,704,350, Williams describes a nutritional microcomputer and method of use in a weight control program. A hand-held device is described which enables a diet log to be recorded, activity levels to be recorded, and diet goals to be set. The Harris Benedict equation is used to calculate the user's daily caloric expenditure. Hence this device and method fails to take into account the change in RMR at the onset of a diet.

In U.S. Pat. No. 5,673,691 to Abrams et al. describe an apparatus to control weight, in which caloric intake levels are adjusted on the basis of changes in the user's body weight. The actual metabolic rate of the user is not determined in the described method of using this device.

In U.S. Pat. No. 4,951,197, Mellinger describes a diet method in which caloric expenditure is calculated from the weight of the person. Individual variations in RMR, and RMR changes during a diet, are not taken into account.

In U.S. Pat. No. 5,890,128, Diaz et al. describe a hand-held calorie computer for use in a weight control program. For weight loss, caloric intake is decreased gradually so as to hopefully avoid abrupt changes in the user's metabolic rate. However, this is not as effective as actually measuring the user's metabolic rate and compensating for changes, as described in embodiments of the present invention.

In U.S. Pat. No. 5,705,735, Acorn describes monitoring the oxygen consumption and carbon dioxide production of a patient on a ventilator, and using the data to assess nutritional requirements. This apparatus not intended to provide information to the patient, but rather to a health professional in attendance, and is not convenient for use in a weight control program.

In U.S. Pat. No. 5,989,188, Birkhoelzer et al. describe the use of indirect calorimetrics in determining the energy balance of a living subject. However, Birkhoelzer et al. do not envision the problematical effects of metabolic change caused by a weight control program on predicting the outcome of the weight control program. They do not describe a weight control program in which the RMR of the subject is monitored through the course of the program, and do not describe how changes in RMR may be used to modify the recommended caloric intake, activity levels, and/or target goals of a weight control program.

SUMMARY OF THE INVENTION

Recently, James R. Mault, invented a low-cost, hand-held, portable indirect calorimeter, referred to as a Gas Exchange Monitor (GEM). This device allows accurate measurement of resting metabolic rate (RMR).

The inventor, James R. Mault, has carried out RMR measurements of persons in a weight control program, and found significant decreases in RMR which cannot be accounted for by weight loss using the Harris-Benedict equation.

The present invention accordingly overcomes the deficiencies of the prior art by measuring the resting metabolic rate (RMR) of a person at intervals, and modifying the RMR component of caloric balance on a dynamic basis to compensate for changes in metabolism which occur during weight control, particularly weight loss.

In the improved weight control program described herein, an indirect calorimeter is used to monitor the RMR of a person at intervals. The RMR values are used to modify the caloric intake and/or activity levels recommended in the weight control program.

The GEM allows direct measurement (not estimates) of a person's RMR at intervals as a person's metabolism changes as a result of a weight control program. RMR changes may be accurately tracked over the course of a weight loss program. RMR may be measured at more frequent intervals (for example, once every 1–5 days) at the start of a weight control program, when metabolism changes may be more rapid. The measurement intervals may be lengthened (for example to every 1–4 weeks) if the person's RMR settles down to an approximately constant value in the course of a weight control program.

In a conventional weight loss program, a person will often become discouraged due to small or non-existent actual weight losses. This is often due to a failure to take RMR changes into account. The present invention allows a person to intelligently navigate a weight control program. Caloric intake may be reduced, activity levels increased, or weight loss expectations may be modified to take into account the changing value of RMR.

In one embodiment of the present invention, a person is provided with a portable computing device, such as a personal digital assistant, with software which enables the device to function as a caloric intake calculator, a caloric expenditure calculator, and a caloric balance calculator. A body weight target may be set, and the initial RMR value used to suggest a caloric intake level and activity level by which the target weight may be achieved in a reasonable time. Soon after the start of the weight control program, the person may be prompted or otherwise reminded to re-determine their RMR level. RMR may change significantly at the beginning of a weight control program. Any significant changes in RMR may be used to re-calculate a reasonable balance of caloric intake, caloric expenditure, and time needed to reach a certain body weight goal. The RMR of the person is measured at intervals through the duration of the weight control program, so as to revise the parameters of the program in a manner consistent with a successful outcome.

BRIEF DESCRIPTION OF THE DRAWINGS

FIGS. 7–12 illustrate example screens provided by software running on a computing device;

DETAILED DESCRIPTION OF THE INVENTION

A person's caloric balance is the difference between their caloric intake (from food, beverages, and other consumables) and their caloric expenditure. Hence, an effective calorie management system has two components. It must monitor caloric intake, and must also monitor caloric expenditure in terms of resting metabolism and physical activity levels.

Diet logging software and activity sensors are known in the art. However, conventional weight control programs do not compensate for changes in resting metabolism during the course of a weight control program. In the improved weight control program described here, an indirect calorimeter is used to measure the RMR of a person at intervals. The values of RMR are then used in a calorie management system.

Recently, James R. Mault, invented an improved indirect calorimeter. This device, sometimes known as the gas exchange monitor (GEM), is preferably used in the improved weight and health control program described here. The improved indirect calorimeter is best described in co-pending U.S. patent application Ser. No. 09/630,398, which is incorporated herein in its entirety by reference. A brief description of the calorimeter follows.

Figure 1:
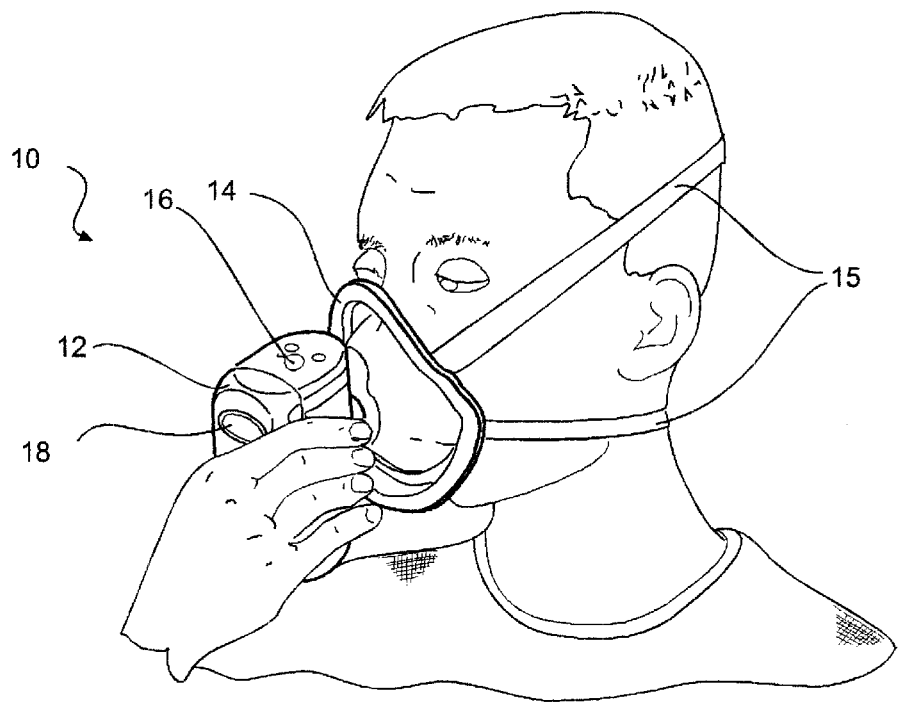
FIG. 1 is a perspective view of a user breathing through an indirect calorimeter.
Figure 2:
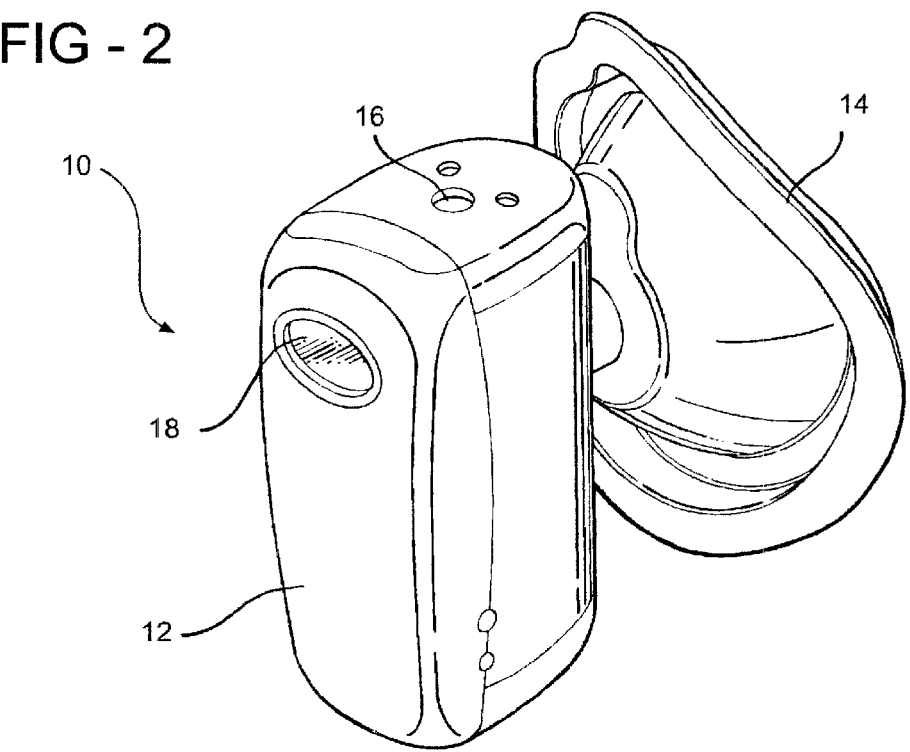
FIG. 2 is a perspective view of an indirect calorimeter.

Referring to FIGS. 1 and 2, the calorimeter according to U.S. patent application Ser. No. 09/630,398 is generally shown at 10. The calorimeter 10 includes a body 12 and a respiratory connector, such as mask 14, extending from the body 12. In use, the body 12 is grasped in the hand of a user and the mask 14 is brought into contact with the user's face so as to surround their mouth and nose, as best shown in FIG. 1. An optional pair of straps 15 is also shown in FIG. 1. With the mask 14 in contact with their face, the user breathes normally through the calorimeter 10 for a period of time. The calorimeter 10 measures a variety of factors and calculates one or more respiratory parameters, such as oxygen consumption and metabolic rate. A power button 16 is located on the top side of the calorimeter 10 and allows the user to control the calorimeter's functions. A display screen is disposed behind lens 18 on the side of the calorimeter body 12 opposite the mask 14. Test results are displayed on the screen following a test.

Figure 3:
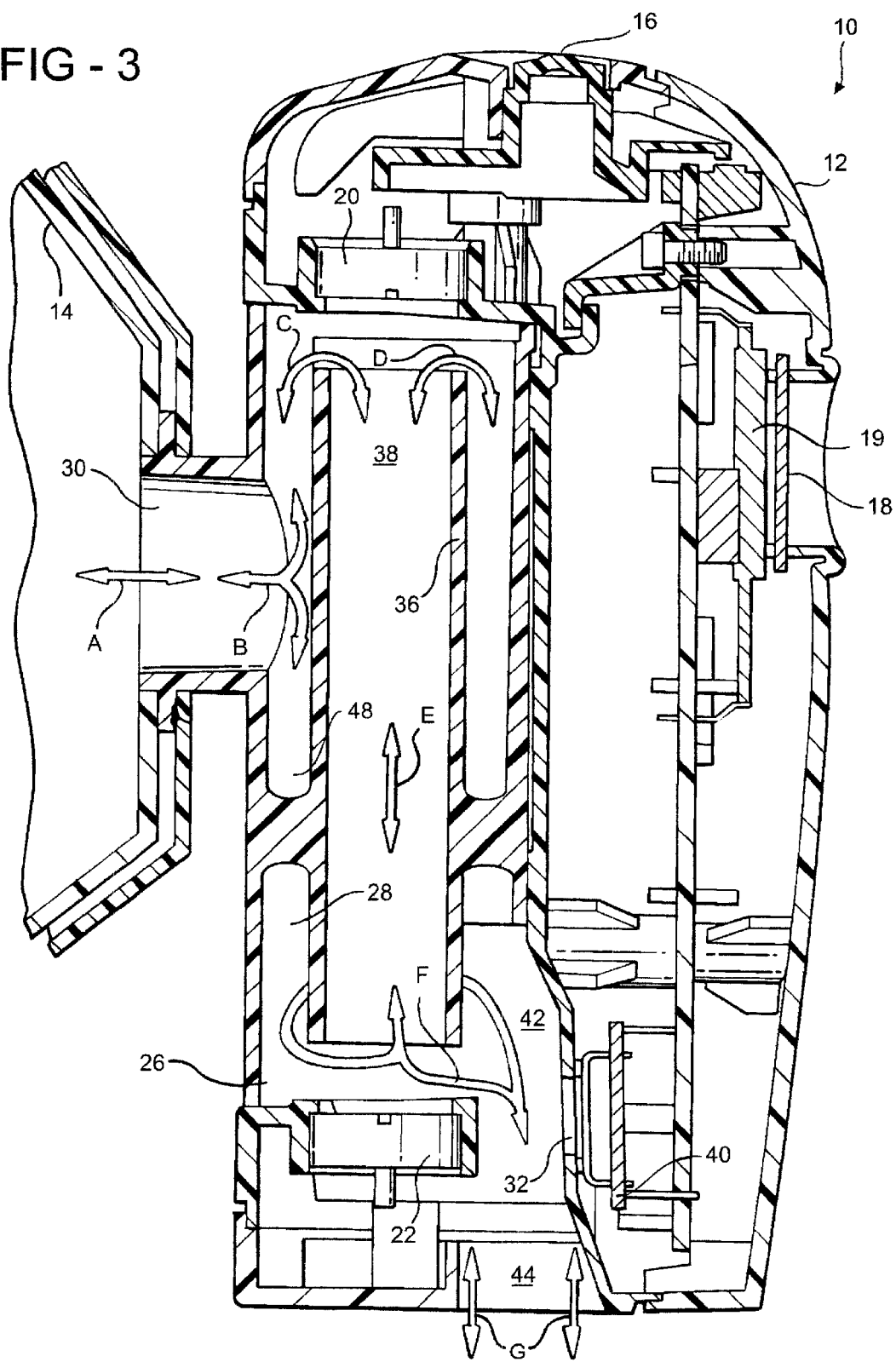
FIG. 3 is a cross-sectional view of an indirect calorimeter.

FIG. 3 shows a vertical cross section of the calorimeter 10. The flow path for respiration gases through the calorimeter 10 is illustrated by arrows A–G. In use, when a user exhales, their exhalation passes through the mask 14, through the calorimeter 10, and out to ambient air. Upon inhalation, ambient air is drawn into and through the calorimeter and through the respiratory connector to the user.

Exhaled air passes through inlet conduit 30, and enters connected concentric chamber 48. Excess moisture in a user's exhalations tends to drop out of the exhalation flow and fall to the lower end of the concentric chamber 48. Concentric chamber 48 serves to introduce the respiration gases to the flow tube 36 from all radial directions as evenly as possible. Exhaled air flows downwardly through a flow path 38 formed by the inside surface of the flow tube 36. Exhaled air enters outlet flow passage 42, via concentric chamber 28, and passes through the grill 44 to ambient air.

Flow rates through the flow path 38 are determined using a pair of ultrasonic transducers 20 and 22. An oxygen sensor 40, in contact with respiratory gas flow through opening 32, is used to measure the partial pressure of oxygen in the gas flow. Integration of oxygen concentration and flow rate allows inhaled oxygen volume and exhaled oxygen volume to be determined. The metabolic rate of the user is determined from the net oxygen consumption; the difference between inhaled and exhaled oxygen volumes. Metabolic rate is determined using either a measured or assumed respiratory quotient (the ratio of oxygen consumption to carbon dioxide production). For a user at rest, the RMR (resting metabolic rate) is determined. The RMR value is shown on display 19.

Preferably, the indirect calorimeter used in embodiments of the present invention comprises a respiratory connector such as a mask or mouthpiece, so as to pass respiration gases as the subject breathes; a flow pathway between the respiratory connector and a source and sink of respiratory gases (such as the atmosphere) which receives and passes the respiration gases; a flow meter configured to generate electrical signals as a function of the instantaneous flow of respiration gases passing through the flow pathway, such as an ultrasonic flow meter; and a component gas concentration sensor, such as a fluorescent oxygen sensor, which generates electrical signals as a function of the instantaneous fraction of gases such as oxygen and/or carbon dioxide in the respiration gases they pass through the flow pathway, such as the indirect calorimeter described above. However, other indirect calorimeters may be used in embodiments of the present invention, for example such as described in U.S. Pat. Nos. 4,917,108; 5,038,792; 5,178,155; 5,179,958; and 5,836,300, all to Mault, which are incorporated herein in their entirety by reference.

Figure 4:
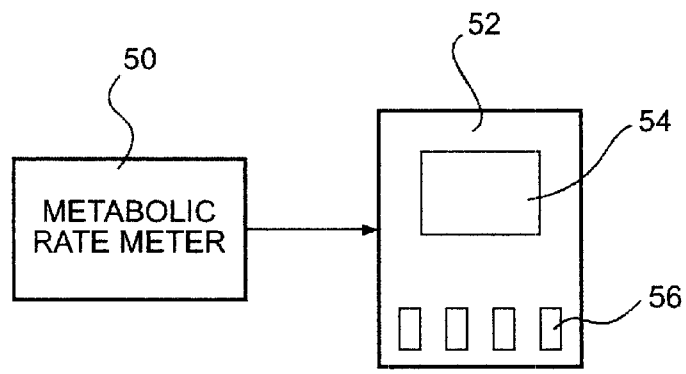
FIG. 4 is a schematic of a system embodiment of the present invention.

FIG. 4 shows a system embodiment of the present invention. We will refer to the person using the system shown in FIG. 4, for example as part of a weight control program, as the user. A device for the measurement of metabolic rate (a metabolic rate meter) 50 provides metabolic rate data relating to the user at intervals to computing device 52. Preferably, an indirect calorimeter (such as that described in U.S. patent application Ser. No. 09/630,398) provides RMR measurements of the user to computing device 52. Device 52 has a display 54 and buttons 56. Buttons 56 may be used for data input (for example navigation through menus, character entry, and the like), changing the operating mode of the device (for example between computer and other functionality such as wireless phone), initiating a voice record, initiating an image capture, or other processes. Data entry may also be achieved using a stylus, touch-screen, roller-jog mechanism, touch-sensitive pad, monitoring eye-movements, voice recognition software, bar-code scanning, optical character recognition, or other convenient data entry mechanism. Preferably, computing device 52 is a personal digital assistant (PDA), but may be any electronic device such as a portable computer; electronic organizer; e-book; wireless phone; pager; wristwatch with added functionality; electronic system such as a system having separate display, entry, and computing modules; any portable/wearable device; a pedometer with added computing functionality; or a desktop computer system.

Figure 5:
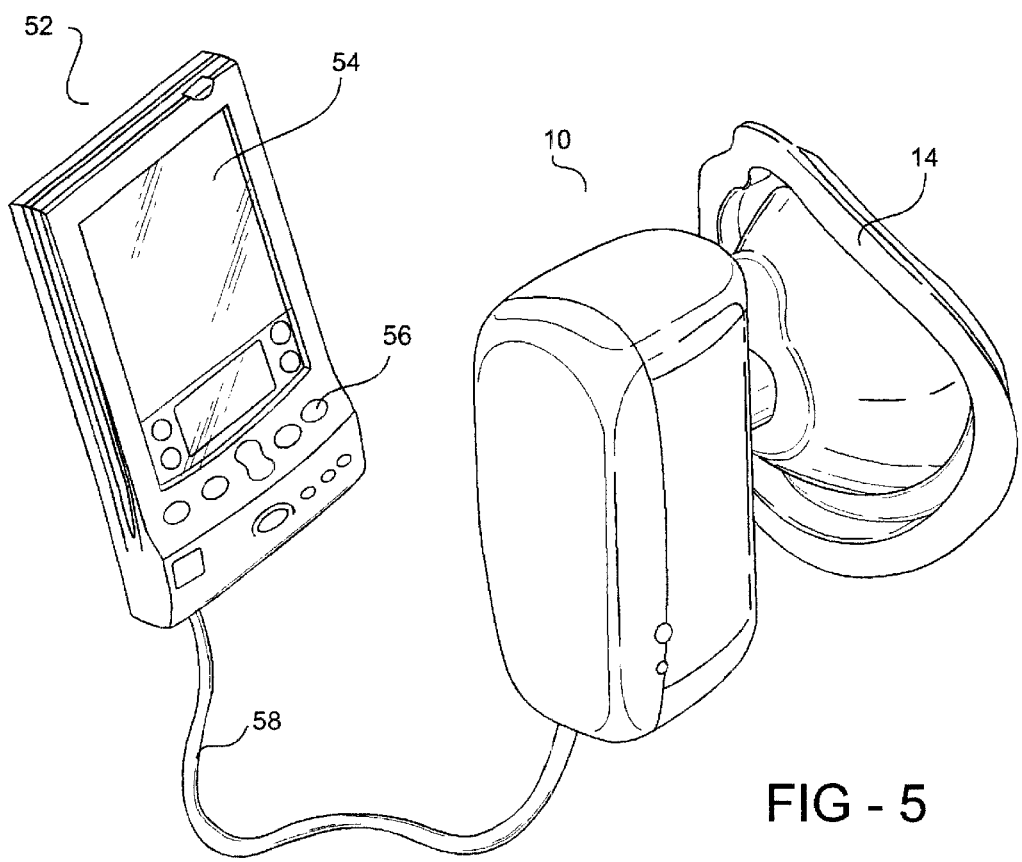
FIG. 5 illustrates an indirect calorimeter in communication with a portable computing device.

FIG. 5 shows an indirect calorimeter 10, with mask 14, in communication with a computing device 52 (with display 54 and data entry buttons 56) using a cable 58. FIG. 5 shows a preferred embodiment of the invention in which a personal digital assistant (PDA) is used as the computing device. Alternatively, a memory module (such as a memory card, memory stick, flash media, or the like) may be used to transfer data from the indirect calorimeter 10 to computing device 52. A wireless communication method, such as an IR beam or Bluetooth wireless protocol, may also be used.

Health management software running on computing device 52 receives the metabolic rate data at intervals, caloric intake data relating to diet, and physical activity level data. The software provides goals and feedback to the user in relation to weight goals, which are modified by changing values in the metabolic rate of the user. Diet logging software and activity sensors are known in the art. However, conventional weight control methods do not compensate for changes in the metabolic rate of the user. The overall capabilities of the software may be summarized in the following list: setting up a user identity by entering name and other information; setting of targets and goals based on information gathered from the user during an initial setup process (weight goals, nutrient targets, health goals, and activity plans); entry of food consumption through a food log with a search capability; entry of activity information combined with a search tool (alternatively using data from an activity sensor); feedback to the user regarding the caloric balance and time dependent logging of body measurements such as resting metabolism, body weight, and body fat percentage; reporting on body measurement trends using graphical display capabilities of the computing device or other device such as an interactive television; and reporting on the nutritional balance of food intake.

Software running on electronic device 52 preferably enables the device to function as a caloric intake calculator (allowing the user to enter data such as food item identity, indicative of food items (including beverages) consumed); a caloric expenditure calculator (allowing caloric expenditure to be determined from data related to physical activity of the user); and allows the device to receive RMR data related to the person at intervals. Activity data may be input by the user, either a numerical value associated with an activity, or by entering the type of activity such as through a menu based system. The user may set health related goals, such as body fat percentage, RMR, or other physiological parameters such as resting heart rate.

Figure 6:
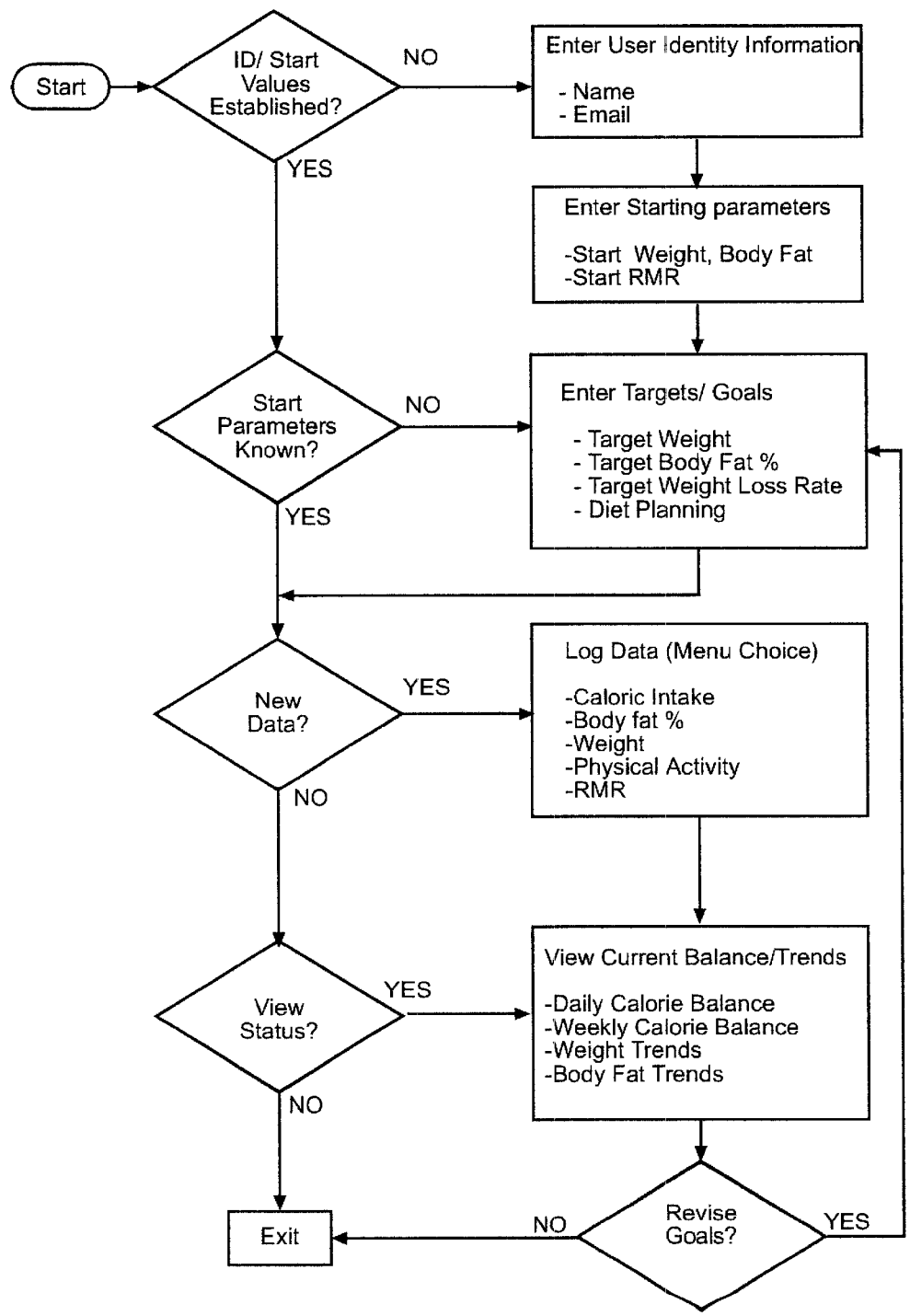
FIG. 6 is a flowchart of software which may run on a computing device, according to embodiments of the present invention.

FIG. 6 shows a schematic illustration of one embodiment of health management software which may run on the computing device 52. At the start of a weight control program assisted by the health management software, the user may enter a set-up procedure in which an identity is established, initial conditions entered, and targets and goals are set. Personal details such as name, e-mail address, birth date or age, gender, and other information such as frame size, and body fat percentage, may be entered into the software. The user then enters weight loss (or weight gain, or weight maintenance goals). The intended rate of weight loss may be: entered, or may default to (for example) one pound per week. The user determines their resting metabolic rate using an indirect calorimeter, preferably the Gas Exchange Monitor invented by James R. Mault. The user also enters their lifestyle, sleep time, and typical exercise level into the device. The software then prepares an estimate or preview of the caloric balance for the person, indicating the caloric expenditure through RMR, caloric expenditure through activity, and caloric intake allowable by consumption. The user may adjust their intended activity level during the course of the weight loss program. The user then selects a customized diet using software on the computing device which allows a preferred distribution of carbohydrate, fat, and protein to be consumed.

During the course of a weight control program, the user enters foods consumed into the software. The food database accessed by the software preferably includes broad categories of food such as meat, vegetables, beverages, etc. and detailed subcategories related to the specific food items and their weight or volumes. Preferably, the food database resides on memory within the computing device 52. The food database may be created or enhanced using data received over a communications network, data received using a cable or wireless link to another device, or by transfer of memory modules. The computing device 52 may be supplied to customers by a weight control business with a food database pre-installed. The software may provide advice on future diet planning, for example suggesting lists of alternative foods which assist the user in achieving a weight loss goal. Activity levels may also be entered through a menu system. The computing device 52 preferably displays information related to the user's caloric and nutritional intakes, and displays trends, caloric balance, and other information relation to goals of the weight loss program.

The computing device then allows the user to view a breakdown of their daily caloric intake and intake of various food groups, vitamins, and minerals, which may be derived from current medical knowledge of healthy diets. After the setup is complete, the user enters diet information through a menu system. The user may select between various food groups to enter the identity of foods consumed. Activity level data is also supplied to the computing device either through user entry or information received from activity sensors. The consumption information and activity levels may then be transferred to a remote computer system. The device may be used as a progress calculator, by which the progress made towards target goals can be compared with initial projections.

By way of illustration, FIGS. 7–12 show a number of example screens which may be shown on the display 54 of computing device 52, provided by health management software running on device 52. FIG. 7 shows two screens in which personal data and starting body parameters may be entered. FIG. 7A shows a personal data entry screen, FIG. 7B shows a starting data entry screen.

Figures 8E, 8F, 9, 10:
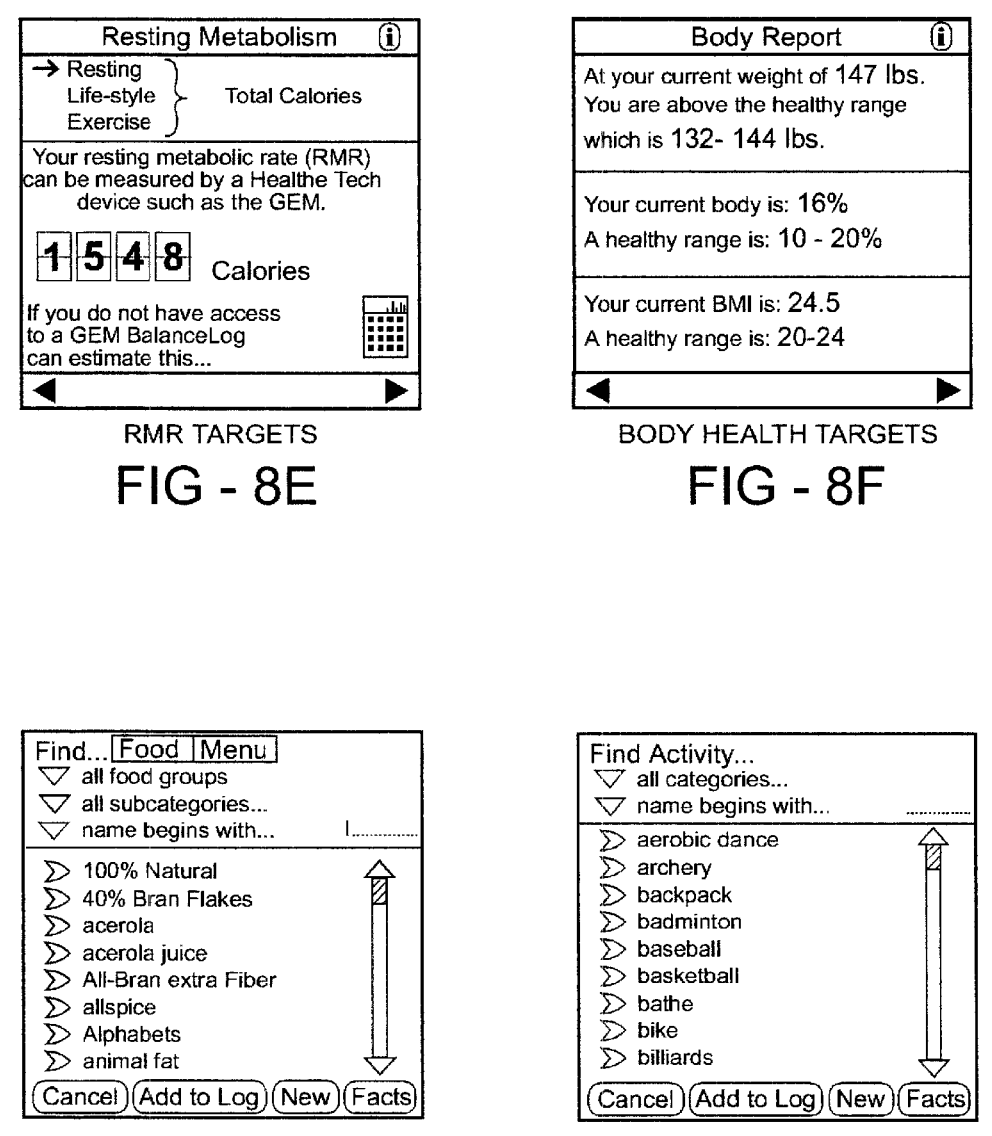

FIGS. 8A–8F show six screens by which weight control, activity, RMR, and nutritional targets may be displayed to the user, and/or adjusted, at the onset of the weight control program. FIG. 8A shows a menu screen from which other displays may be chosen, FIG. 8B shows a daily caloric balance target, FIG. 8C shows a daily nutrition target, FIG. 8D shows a screen in which activity levels may be entered, FIG. 8E shows the daily calories burned by the user's RMR, and FIG. 8F shows body health targets.

FIG. 9 shows a food database screen, allowing the user to enter diet choices. Names may be entered directly (by entering the first few letters), or through a menu system. Food products may be sorted by category or brand name. Also, the computing device 52 may be equipped with a bar-code scanner by which product codes may be scanned off food packages, and the information obtained entered into a diet log database.

FIG. 10 shows an exercise database screen, allowing the user to enter or estimate activity levels. Activities may be entered directly by entering the first few letters of the name, or by selecting from menu options. An exercise database is preferably stored within the memory of the computing device 52, which relates activities to caloric expenditure.

Figure 11A:
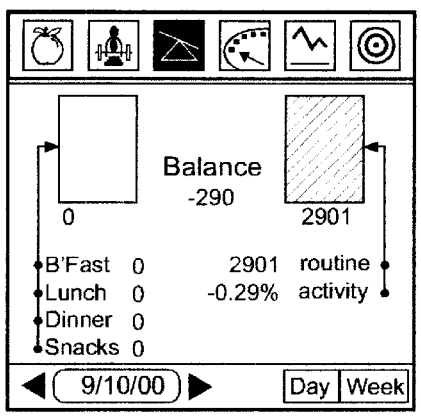
Figure 11B:
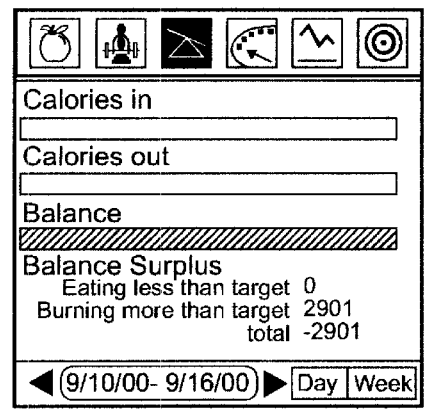

FIG. 11 shows daily (FIG. 11A) and weekly (FIG. 11B) balance screens, allowing the user to view their caloric balance on a daily or weekly basis.

Figure 12A:
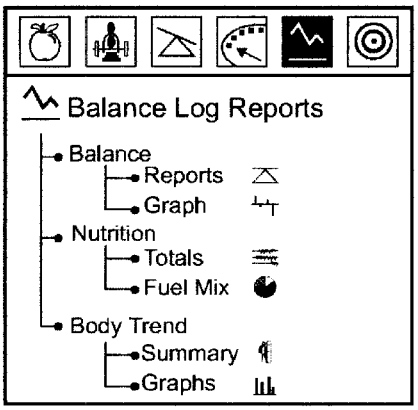
Figure 12B:
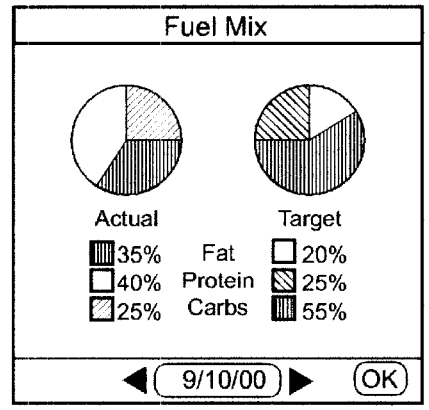
Figure 12C:
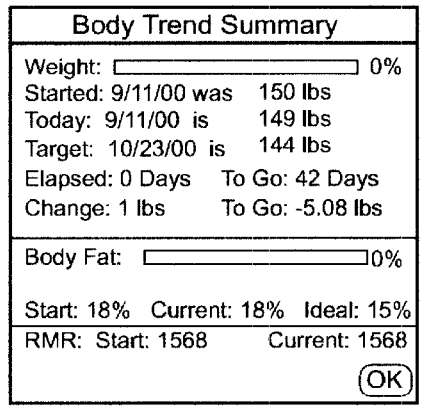

FIG. 12 shows three example screens, by which status aspects of the weight loss program may be observed. FIG. 12A shows a balance log report screen, allowing the options of tabular and graphical display of trends. FIG. 12B illustrates a screen showing nutrition breakdown, and FIG. 12C illustrates a screen showing body trends.

Weight control related data may be compared with previous day's, week's, or month's data, and trends determined. The day's caloric intake may be compared with that allowed for the successful achievement of the target weight. Changes that may relate to medical problems may be diagnosed, and the user's physician notified. The status of a person's caloric balance may be indicated by icons or screen displays based on various themes. For example, using a weather scheme, a cloud may be used to indicate caloric intake greater than caloric expenditure (which we may call a negative caloric balance), and a sunny sky used to indicate a caloric intake less than caloric expenditure (which we may call a positive caloric balance). Using a banking theme, an array of banknotes or other wealth representation may be used to show indicate caloric intake less than caloric expenditure, whereas pennies, a bill, or other representation of poverty may be used to indicate a caloric intake greater than caloric expenditure.

The software running on the electronic device 52 is preferably adapted to receive RMR data at intervals. Intervals may be frequent (such as an RMR measurement daily or every 2–3 days) during the early stages of the program, and less frequent (such as an RMR measurement every week, 2–3 weeks, or monthly) during later stages when metabolic changes would be expected to be smaller over a given time period. The software may be used to prompt the user to measure RMR, based on the stage of the weight control program, changes in other monitored parameters, and previous RMR changes. The time intervals between RMR measurements may be increased in length after an initial period has elapsed. For example, if RMR changes are expected (for example, from studies) to occur largely in an initial two week period of a health monitoring program, in which the user's caloric intake is initially reduced a certain percentage, then RMR measurements may be made every 2 days during this initial period, during which goals may be revised according to the actual RMR change. For example, a greater weight loss goal may be suggested if RMR does not fall, or increases due to activity. The initial period (for frequent RMR testing) may be restarted if caloric intake is modified significantly. However, if RMR settles to a stable level during the initial period, then the time intervals between RMR determination may be increased, e.g. to bi-weekly, after the initial period has elapsed. Intervals may also be adjusted continuously based on the actual changes in RMR, for example the next RMR measurement may be scheduled at a future time at which RMR may be predicted to have fallen by some value (perhaps defaulting to a maximum time interval if RMR is stable).

The health and fitness of the user can be monitored by monitoring some combination of body weight, RMR, body fat percentage, and other physiological parameters. The present invention provides a method of managing the health of a user by determining the resting metabolism of the user using an indirect calorimeter at suitable intervals; recording data indicative of foods consumed by the user over time; recording data indicative of activities performed by the user over time; processing the food data to determine caloric intake; and processing the activity data and the resting metabolism to determine caloric expenditure. Hence a caloric balance can be determined for the user, as described above. Other physiological parameters may be monitored in conjunction with diet and activity levels. Processing steps are preferably carried out using the computing device 52, but other devices in communication with device 52 may also provide additional data and processing support.

Figure 13:
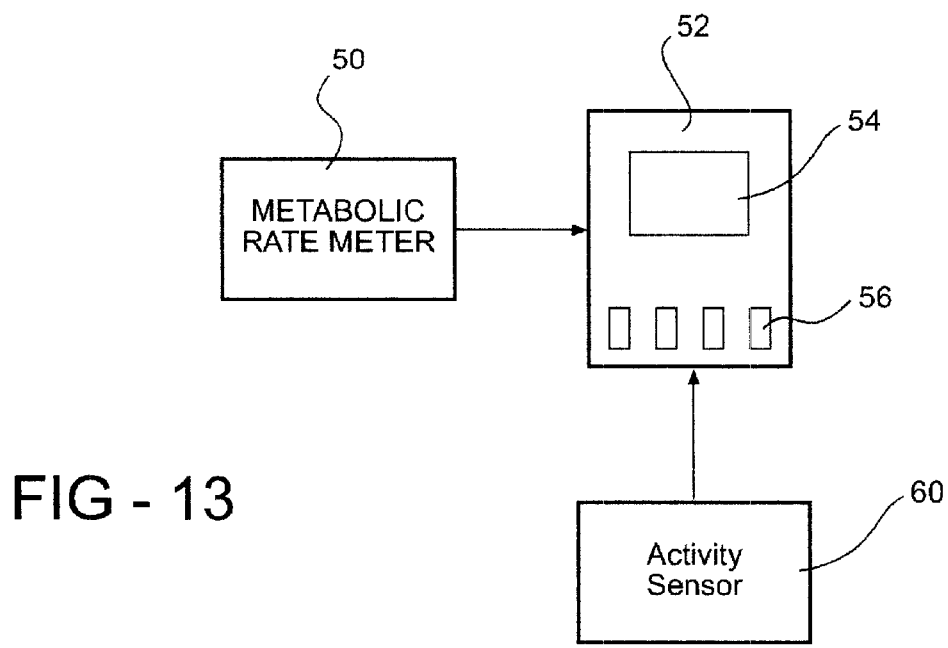
FIG. 13 is a schematic of a system embodiment of the present invention, including an activity sensor.

FIG. 13 shows another embodiment of the present invention. As described above, computing device 52 receives data at intervals from indirect calorimeter 50, relating to the resting metabolic rate of the user. The computing device also receives physical activity data from activity sensor 60 regarding the user. Preferably, this is a body or clothing mounted accelerometer, providing a signal related to physical activity. Such devices are well known to those skilled in the exercise arts. Accelerometers may provide a signal related to subject movement along one or more axes. The signal may be correlated with an increased metabolic rate associated with the physical activity by calibrating the sensor 60 with an indirect calorimeter. This has been described in pending U.S. application to James R. Mault, filed Oct. 6, 2000, which is herein incorporated by reference in its entirety.

Figure 14A:
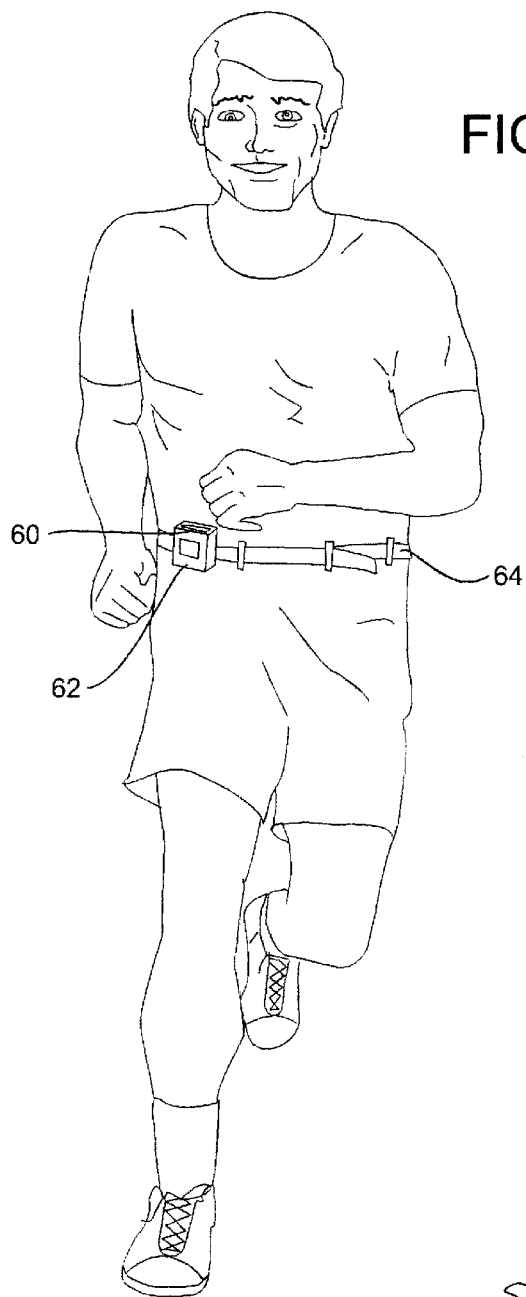
FIGS. 14A and 14B show a user carrying an activity sensor.
Figure 14B:
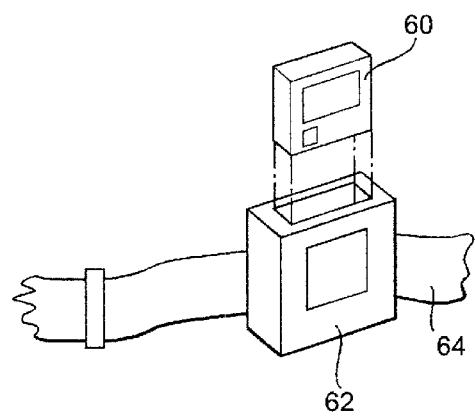

FIGS. 14A and 14B show an activity sensor 60 carried in a holder 62 held on belt 64 around the user. The activity sensor may be in the form factor of a module which is plugged into the computing device 52, which gives the device 52 the functionality of a pedometer or other activity sensor. This has been described more fully in pending U.S. patent application Ser. No. 09/669,125, herein incorporated in its entirety by reference. For example, in the case that device 52 is a PDA, the activity sensor 60 may be in the form of a module, harness, frame, or card which plugs into, docks with, or otherwise interfaces with a PDA and provides the PDA with an additional pedometer function.

The activity module may be clipped onto clothing, a belt, strap, or be adhered to the user's body. The activity module may display data which can be entered manually into device 52, such as a number related to cumulative activity. In a preferred embodiment, device 60 transmits activity related data to device 52 using a wireless link such as the Bluetooth protocol, or an IR method. A cable or other interface may also be used.

Figure 15:
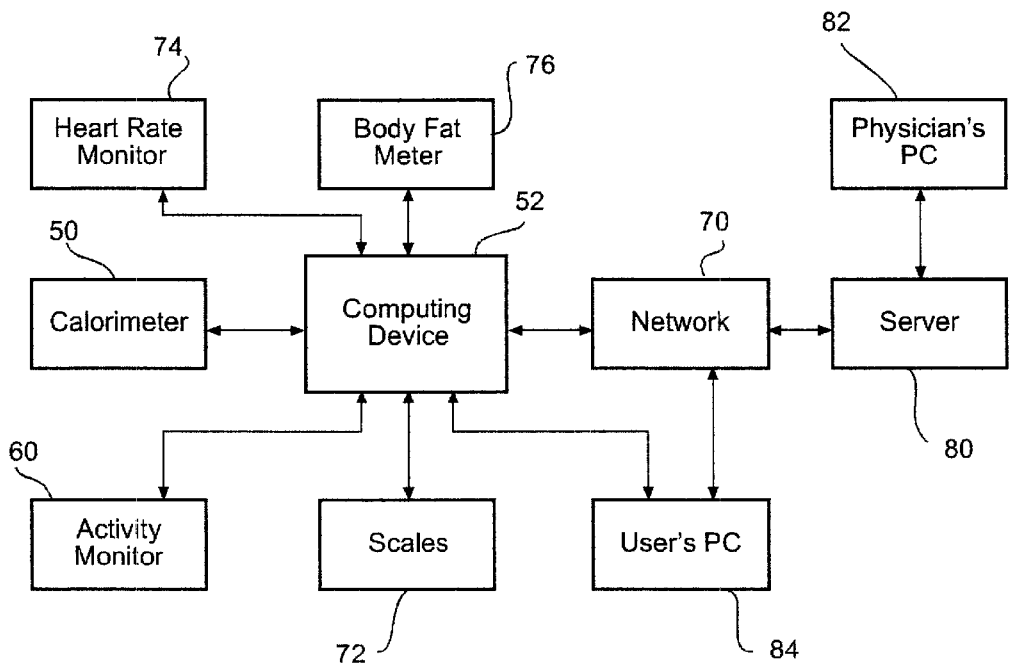
FIG. 15 is a schematic of another system embodiment of the present invention.

FIG. 15 illustrates another system embodiment of the present invention. Computing device 52 receives data at intervals from indirect calorimeter 50. Device 52 also receives data from activity sensor 60 to determine the level of physical activity of the user. A heart rate monitor 74 may also be used. The user's weight, determined by scales 72, is also entered into the computing device at intervals. The body fat percentage of the user is determined at intervals using body fat meter 76. The scale 72 and body fat meter 76 may be combined into a single device such as scales providing electrodes for bioimpedance measurements, such as those available commercially from Tanita and other companies.

Alternatively, body fat meter 68 and computing device 52 may be combined into a single device, or the body fat meter 68 may be an accessory module to computing device 52. For example, computing device 52 may provide electrodes and measurement circuitry so as to determine body fat using bioimpedance. This has been described more fully in pending U.S. provisional application Serial No. 60/219,069, filed Jul. 18, 2000, herein incorporated in its entirety by reference. This and other physiological monitors have been described more fully in pending U.S. patent application Ser. No. 09/669,125, incorporated herein in its entirety by reference.

Caloric data is received by health management software on computing device 52. Device 52 may be connected to a communications network 70, such as the Internet. In the embodiment that computing device 52 is a PDA, the PDA preferably has a wireless connection to the Internet. The PDA may also be docked or otherwise brought into communications with another device having a link to the communications network. For example, the PDA may be docked with a desktop personal computer having Internet access.

Data collected by device 52, related to the health and weight status of the user, may be transmitted via communications network 70 to a remote computer system (for example, a server system) 80. Remote computer system 80 comprises memory for storing information related to the user on a database. Remote system 80 may also have software for provision of feedback to the user. For example, a computer expert system may be used to provide feedback to the user. The user or other authorized person may access information on the database related to the user, for example through an Internet website. For example, information related to the user may be accessed by a physician, dietician, nutritionist, fitness adviser, physician, other health professional, or other lifestyle expert. A physician may use a personal computer 82 linked to the remote computer system 80 (possibly through communications network 70). In another example, a nutritionist may access the database of foods consumed by the user and weight trends, and provide feedback to the user in terms of foods to avoid and alternatives to previously consumed items of poor nutritional value. A weight control or health management business may provide computing devices such as 52 to multiple users, and have the multiple users communicate data relating to their health or weight management programs to one or more remote computer systems (such as Web servers), so that an employee of the business or other authorized person may access data of multiple users.

A weight control business may provide personal digital assistants, or software customized to run on personal digital assistants, to a large number of consumers. The weight loss business may provide an interactive website accessible through a communications network such as the Internet. The website may be used by the consumers for the storage, display, and analysis of data collected. The collected data may also be used to monitor trends amongst the consumer base, hence enabling the improvement of advice given to any individual consumer.

The user may carry or otherwise interact with one or more physiological monitors. Physiological parameters and monitors may include heart rate (for example using sensor 66), respiration rate, electrocardiograms, body temperature, and other parameters.

Figure 16:
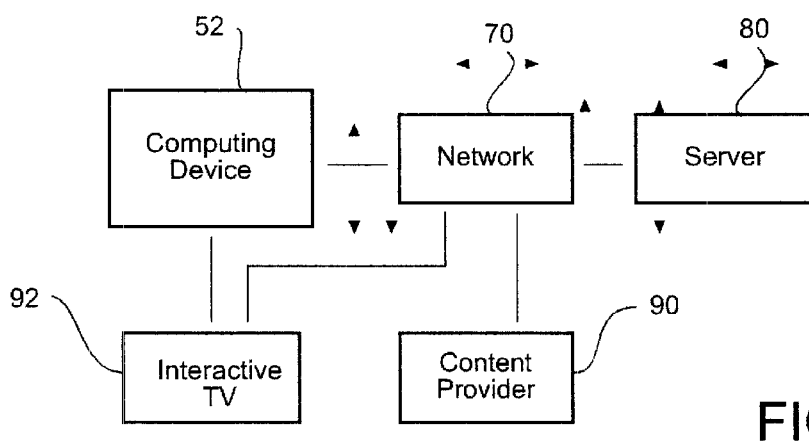
FIG. 16 is a schematic of another system embodiment, by which improved feedback may be provided to the user.

FIG. 16 shows a system embodiment by which improved feedback may be provided to the user. Computing device 52 is used to collect information regarding the user, such as metabolic rate, diet log, activity levels, and physiological parameters, as described above. We will refer to this collectively as lifestyle information. Lifestyle information is stored within a database on remote computer system (for example, a server system) 80. Lifestyle data is transmitted from computing device 52 to computer system 80 through communications network 70, preferably the Internet. The computer system 80 analyzes the lifestyle data and determines appropriate feedback. The feedback is provided either by computer system 80, or by another feedback provider 90.

The user may view feedback on the display of computing device 52, but preferably views feedback on entertainment device 92, preferably an interactive television. Device 92 may also be a personal computer, web access device, web TV, or audio-visual entertainment device.

The computing device 52 may also be used to transmit weight control related data to the interactive television or other device connected to communications network 70 by any convenient means. The Bluetooth protocol may be used for all short range communications and data transfer described in this specification. IR beams, cables, optical methods, memory module transfer, electrical interfaces, and ultrasound may also be used. In embodiments in which the computing device 52 is a PDA or other hand-held device, it may also be used as a remote control to control entertainment devices.

For example, suppose information provided by an indirect calorimeter indicates that the user's metabolic rate has fallen during the weight control program. It would be advantageous for the user to engage in enhanced levels of physical activity in order to increase their resting metabolic rate. Based on the user's demographic data (age, gender), weight, and previous levels of activity, an exercise program can be devised for the user. A video program may be compiled from various appropriate segments and viewed by the user on the entertainment device.

The format and style of the feedback may be varied to optimize the response of the user. For example, the format might be in a news style, containing phrases such as "In breaking news, doctors have shown that increased exercise leads to enhanced resting metabolism and diet success." The style and tone of the feedback may be matched to an optimum response of the user using the results of previous testing, questioning, previous success or failure at weight control, or other information regarding the user. For example, the feedback may be humorous, serious, nagging, etc. An authority figure, such as a simulation of the president, may be used to provide feedback to the user.

The remote server 80 preferably has an application program for receiving, storing, displaying and analyzing the information from the PDA relative to the user's physiological status, activities, and consumption. The information may be transmitted at intervals to health care professionals overseeing the weight loss program such as nutritionists, physicians and the like. Based on communications from the health care professionals to the website, and/or analysis performed on the website, messages could be transmitted by the server via the communications network to the PDA for display by the PDA to the patient. The messages could deal with the patient's program and could include messages as to modifications in the patient's conduct, including tests to be conducted or intervals for such tests, and information related to food consumption. The messages may include encouragement or criticism of past results. The system provides regular oversight which is highly successful in other commercial weight loss programs. The patient's response is enhanced by the knowledge that their progress will be communicated either to a health professional or to a computer program overseeing their progress. The computing device 52 may also receive information on the user's state of mind, for example relative to their happiness with the plan's diet and feelings of success of the program.

Preferably, the user records food and beverage consumption on the computing device 52 immediately after consumption. However, informal records may be stored on the computing device, such as voice records, image records, notes, data from barcode scanning, data from optical character recognition scanning, and used at a future time to create a formal diet log. A formal diet log may be created by the user or by other authorized persons with access to the data. For example, a weight control business may provide employees to create a formal diet log from informal records captured by the user of the system.

Electrical signals sensed by physiological monitors may be transferred to the computing device 52 through either wired or RF or other wireless links. The physiological monitors could incorporate connectors to receive removable memory sticks or cards such as flash memory or battery supported memory. These sticks or cards could be connected to the physiological monitors during monitoring and later removed and inserted into the PDA. The same memory module may be used with a variety of physiological monitors or employing a common data format.

Data collected by a portable computing device may be transferred to a portable device carried by a health care professional, such as a nutritionist, allowing the nutritionist to review the data on their own device and hence provide improved feedback and advice to the user.

Figure 17:
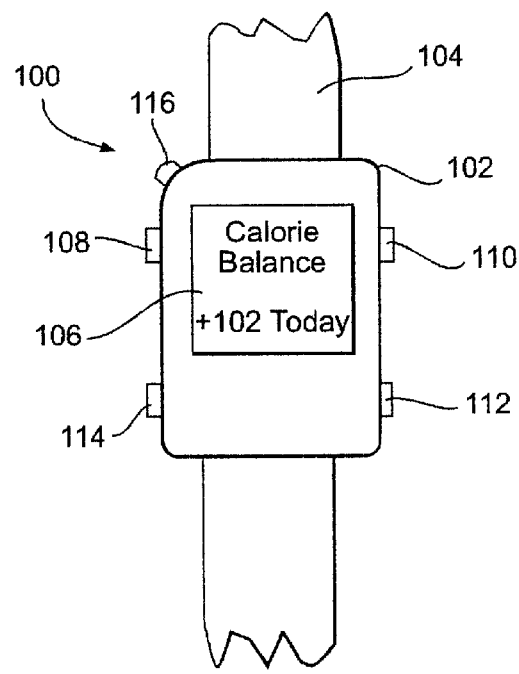
FIG. 17 shows a wrist-mounted computing device.

FIG. 17 shows a wrist-mounted device, which may be used as the computing device 52 in one embodiment of the present invention. This has been described more fully in pending U.S. provisional application Ser. No. 60/207,051, the contents of which are incorporated in its entirety by reference. A person wears the wrist-mounted device, shown generally at 100, which resembles a watch. The device has main housing 102, and strap 104 to place around the user's wrist. A display 106 is used to show time, caloric balance, a diet input menu screen, an activity input menu screen, and an RMR input screen. A mode button 108 is used to change display mode. Buttons 110, 112, and 114 may be used to navigate through menu option choices, and select data items to record. The caloric balance for a person is related to the caloric intake compared with the caloric expenditure as previously described. Bar codes on prepackaged foods may be read by a bar code reader 116 associated with the housing 102 of the wrist-mounted device, and bar code data converted to nutrition data using a database. If a person is eating prepackaged foods from a limited selection, for example, meals supplied as part of a weight control program, the database relating bar code data to nutrition information may be conveniently stored within memory within the housing of the wrist-mounted device. An enhanced database may be stored on a remote server in communication with the wrist mounted device through a communications network.

Figure 18:
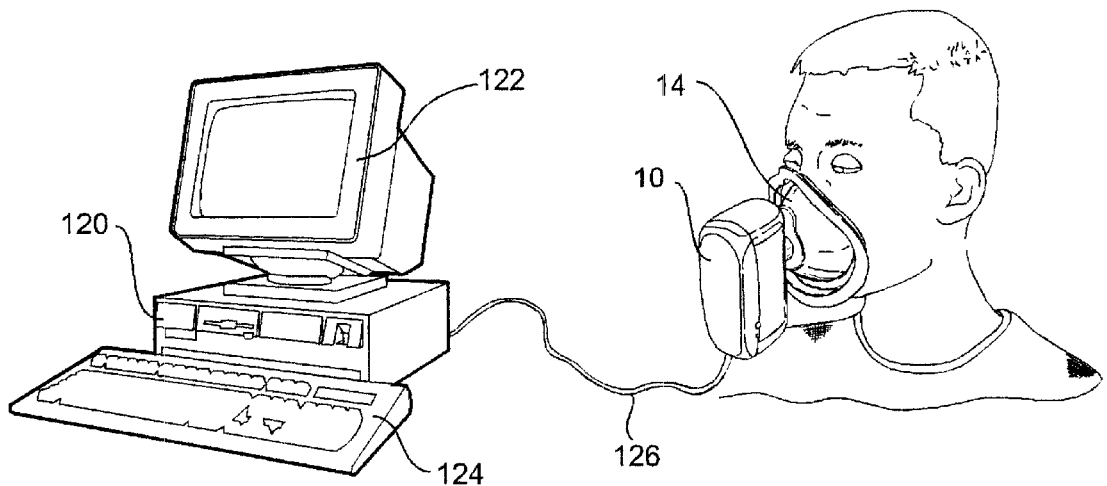
FIG. 18 illustrates a user breathing through an indirect calorimeter in communication with a desktop computer.

Access to an indirect calorimeter may be provided at a physicians office, nutritionists office, fitness center, retail center, and the like. FIG. 18 shows a configuration suitable for use at a fitness center. FIG. 18 shows a user breathing through mask 14 of indirect calorimeter 10, which is in electrical communication with a desktop computer 120 provided by the fitness center. The fitness center may provide calorimeter 10, or the user may provide the calorimeter or disposable elements such as mask 14. The user, a customer of the fitness center, enters login information into the personal computer and breathes through the indirect calorimeter so as to measure their metabolic rate and store this in a computer system belonging to the fitness center, possibly a remote server in communication with PC 122. The fitness center may maintain a health and fitness database related to the user, containing data such as weight, RMR, diet information, and exercise performed. The fitness center may provide advice and feedback regarding the user's progress towards weight goals and fitness goals. An increased metabolic rate is indicative of an increased level of muscle mass, or reduced fat percentage for a constant body weight, hence is a desirable goal for users of the fitness center. The processor from the previous described embodiment of the indirect calorimeter (U.S. patent application Ser. No. 90/630,398) may be removed and signals from the transducers within the flow path of the indirect calorimeter used to send signals to a separate module which may be placed between the indirect calorimeter and personal computer. This reduces the weight of the device placed on the user's face, and also reduces sources of heat near the flow path which may reduce the accuracy of gas flow sensors. Data collected by exercise machines located within the fitness center may also be added to a database regarding the user stored on the computers of the fitness center.

As will be clear to those of skill in the art, the above-described embodiments of the present invention may be altered in various ways without departing from the scope or teaching of the present invention. It is the following claims, including all equivalents, which define the scope of the invention.

I claim:

1. A method of managing the health of a user, said method comprising the steps of:
   determining at intervals the resting metabolic rate of the user using an indirect calorimeter, wherein the interval for determining the resting metabolic rate of the user is adjusted based on changes in the user's resting metabolic rate over time;
   transmitting a signal representative of the user's metabolic rate to a computing device operatively in communication with the indirect calorimeter, wherein the computing device includes a processor, a memory, an input mechanism, and a display;
   providing data indicative of food consumed by the user over a predetermined period of time to the computing device;
   providing data indicative of activities performed by the user over the predetermined period of time to the computing device;
   using the food consumption data to determine caloric intake;
   using the activity data, caloric intake and the resting metabolic rate to determine a caloric expenditure of the user over the predetermined period of time; and
   providing the user with their caloric expenditure for the predetermined period of time.

2. The method according to claim 1, further including the step of comparing the caloric intake and the caloric expenditure to determine a caloric balance.

3. The method according to claim 2, further including the step of displaying the caloric intake, the caloric expenditure, and the caloric balance for the predetermined period of time on the computing device.

4. The method according to claim 1, further including the step of providing a food database in a memory of the computing device containing nutritional data for a plurality of foods and using the nutritional data from the database in determining caloric expenditure.

5. The method according to claim 1, further including the step of establishing a health management goal and using the caloric intake, the activity level, and the caloric expenditure to measure progress towards the goal.

6. The method according to claim 5, further including the step of adjusting the goal, by the user, based on the progress.

7. The method according to claim 1, further including the step of transmitting data related to food consumption and activity performance to a remote location, analyzing the transmitted data in measuring progress towards a health management goal, and providing feedback to the user regarding the progress towards the health management goal.

8. The method according to claim 7, wherein the remote location is a remote computer operable to analyze the transmitted data and provide feedback.

9. The method according to claim 1, further including the step of prompting the user at a predetermined interval to measure their resting metabolic rate using the indirect calorimeter.

10. The method according to claim 1, wherein the step of providing data indicative of an activity performed includes wearing an activity sensor by the user and transmitting a signal indicative of the user's movement from the activity sensor to the computing device.

11. The method according to claim 1, wherein the computing device is a personal digital assistant (PDA).

12. A method of managing the health of a user, said method comprising the steps of:
   establishing a health management goal by the user;
   determining at intervals the resting metabolic rate of the user using an indirect calorimeter; wherein the interval for determining the resting metabolic rate of the user is adjusted based on changes in the user's resting metabolic rate over time;
   transmitting a signal representative of the user's metabolic rate to a computing device operatively in communication with the indirect calorimeter, wherein the computing device includes a processor, a memory, an input mechanism, and a display;
   providing data indicative of food consumed by the user over a predetermined period of time to the computing device;
   providing data indicative of activities performed by the user over the predetermined period of time to the computing device;
   using the food consumption data to determine caloric intake;
   using the activity data, caloric intake and the resting metabolic rate to determine a caloric expenditure of the user over the predetermined period of time;
   using the caloric intake, the activity level, and the caloric expenditure to measure progress towards the goal by the user; and
   providing the user with their caloric intake, activity level, caloric expenditure and progress towards the goal on the display of the computing device.

13. The method according to claim 12, further including the step of comparing the caloric intake and the caloric expenditure to determine a caloric balance.

14. The method according to claim 13, further including the step of displaying the caloric intake, the caloric expenditure, and the caloric balance for the predetermined period of time on the computing device.

15. The method according to claim 12, further including the step of providing a food database in a memory of the computing device containing nutritional data for a plurality of foods and using the nutritional data from the database in determining caloric expenditure.

16. The method according to claim 12, further including the step of adjusting the goal, by the user, based on the progress.

17. The method according to claim 12, further including the step of transmitting data related to food consumption and activity performance to a remote location, analyzing the transmitted data in measuring progress towards a health management goal, and providing feedback to the user regarding the progress towards the health management goal.

18. The method according to claim 17, wherein the remote location is a remote computer operable to analyze the transmitted data and provide feedback.

19. The method according to claim 12, further including the step of prompting the user at the predetermined interval to measure their resting metabolic rate using the indirect calorimeter.

20. The method according to claim 12, wherein the step of providing data indicative of an activity performed includes wearing an activity sensor by the user and transmitting a signal indicative of the user's movement from the activity sensor to the computing device.

21. A health management system for a user comprising;
   an indirect calorimeter for determining the resting metabolic rate of the user at an interval, wherein the interval is adjusted based on changes in the user's resting metabolic rate; and
   a computing device operatively in communication with the indirect calorimeter that receives the user's resting metabolic rate, receives food intake by the user over a predetermined period of time and determines caloric intake, receives activities performed by the user over the predetermined period of time, correlates the user's resting metabolic rate, caloric intake and activity level to determine the user's caloric expenditure, and determines the user's caloric balance from the caloric intake and the caloric expenditure, wherein the computing device includes an input mechanism, a memory, a processor, and a display.

22. The system according to claim 21 wherein the computing device is a personal digital assistant (PDA).

23. The system according to claim 21 wherein the indirect calorimeter operatively communicates with the computing device via a wired communications link.

24. The system according to claim 21 wherein the indirect calorimeter operatively communicates with the computing device via a wireless communications link.

25. The system according to claim 21 wherein the user uses the input mechanism to provide a health management goal that is maintained in the memory of the computing device.

26. The system according to claim 21 wherein a food database containing nutritional data for a plurality of foods is maintained in the memory of the computing device.

27. The system according to claim 21 wherein a health management software program in the memory of the computing device uses the metabolic rate data, caloric intake data and physical activity level data to provide the user information relating to the user's progress towards a predetermined health management goal.

28. The system according to claim 21 wherein the health management software modifies the goal set by the user based on changes in at least one of the metabolic rate, caloric balance, progress towards the goal, activity level or caloric intake of the user.

29. The system according to claim 21, wherein the health management software modifies the interval for measuring the resting metabolic rate of the user based on changes in the metabolic rate of the user over time.

30. The system as set forth in claim 21, wherein the indirect calorimeter includes:
   a respiratory connector configured to be supported in contact with the subject so as to pass respiration gases as the subject breathes;
   a flow pathway operable to receive and pass the respiration gases, the flow pathway having a first end in fluid communication with the respiratory connector and a second end in fluid communication with a source and sink of respiratory gases;
   a flow meter configured to generate electrical signals as a function of the instantaneous flow of respiration gases passing through the flow pathway; and
   a component gas concentration sensor operable to generate electrical signals as a function of the instantaneous fraction of the component gas in the respiration gases as the gases pass through the flow pathway.

31. The system as set forth in claim 30, wherein the component gas sensor is an oxygen sensor.

32. The system as set forth in claim 21, further including an activity sensor Operatively in communication with the computing device via a communications link for sensing activity by the user.

33. The system as set forth in claim 32, wherein the activity sensor includes an accelerometer for sensing movement by the subject.

34. The system as set forth in claim 21, whereby the intervals over time are increased in length after an initial period has elapsed.

35. The system as set forth in claim 21, further comprising a means for transmitting data related to food intake and activity level to a remote location that analyzes the transmitted data for measuring progress towards the health management goal, and provides feedback to the user regarding the progress towards the health management goal.

36. The method according to claim 35, wherein the remote location is a remotely located computer operable to analyze the transmitted data and provide feedback to the user.

37. A system of health management for a user comprising:
   means for measuring resting metabolic rate of the user by indirect calorimetry at intervals;
   means for transmitting a first signal representative of resting metabolic rate to a means for receiving said first signal of resting metabolic rate;
   means for receiving a second signal representative of food consumed by the user over a predetermined period of time;
   means for determining caloric intake from said second signal of food consumed;
   means for receiving a third signal representative of activity level of the user for the predetermined period of time;
   means for determining a caloric expenditure for the predetermined period of time from the first signal of resting metabolic rate, caloric intake and third signal of activity level;

means for displaying the caloric expenditure to the user; and means responsive to the caloric expenditure for adjusting the interval for measuring resting metabolic rate based on changes in the user's resting metabolic rate over time and transmitting the adjusted interval to the user.

38. The system as set forth in claim 37, wherein the means for measuring resting metabolic rate is an indirect calorimeter comprising:

a respiratory connector configured to be supported in contact with the subject so as to pass respiration gases as the subject breathes;

a flow pathway operable to receive and pass the respiration gases, the flow pathway having a first end in fluid communication with the respiratory connector and a second end in fluid communication with a source and sink of respiratory gases;

a flow meter configured to generate electrical signals as a function of the instantaneous flow of respiration gases passing through the flow pathway; and a component gas concentration sensor operable to generate electrical signals as a function of the instantaneous fraction of the component gas in the respiration gases as the gases pass through the flow pathway.

39. The system according to claim 38, wherein the component gas sensor is an oxygen sensor.

40. The system according to claim 37, wherein the means for determining caloric intake includes a food database containing nutritional data for a plurality of foods.

41. The system according to claim according to claim 37, wherein the means for determining caloric expenditure is a caloric intake calculator operable to receive the data indicative of food consumed and to retrieve nutritional data from the database corresponding to the data indicative of food consumed, the calculator further operable to tally the nutritional data over a period of time.

42. The system according to claim 37, wherein the means for receiving the first signal, means for receiving the second signal, means for determining caloric intake, means for receiving the third signal, means for determining caloric expenditure, display means, and adjusting means are integral to a personal digital assistant (PDA).

43. The system according to claim 37 further comprising a means for providing the user access to a remote computer system through a communications network so as to allow the person to communicate with the remote computer through the communications network, so that at least the user may view data relating to their health management plan stored on the remote computer system through the communications network.

44. The system according to claim 37 further comprising an activity sensing means disposed on the user and operatively in communication via a communication link for sensing activity by the user.

45. The system as set forth in claim 44, wherein the activity sensing means includes an accelerometer for sensing movement by the user.

46. The system as set forth in claim 37, further comprising a means for determining a caloric balance using the caloric intake and total caloric expenditure for the predetermined period of time.

47. The system as set forth in claim 46, further comprising a means for receiving a health management goal from the user, and a means for comparing the goal to the caloric balance to determine progress toward the goal.

48. The system as set forth in claim 37 further comprising a means for transmitting data related to food intake and activity level to a remote location that analyzes the transmitted data in measuring progress towards the health management goal, and provides feedback to the user regarding the progress towards the health management goal.

49. The system as set forth in to claim 48, wherein the remote location is a remotely located computer operable to analyze the transmitted data and provide feedback.

\* \* \* \* \*

UNITED STATES PATENT AND TRADEMARK OFFICE
CERTIFICATE OF CORRECTION

PATENT NO.    : 6,478,736 B1
DATED         : November 12, 2002
INVENTOR(S)   : Mault It is certified that error appears in the above-identified patent and that said Letters Patent is hereby corrected as shown below:

<u>Title page,</u>
Item [56], References Cited, replace "4,031,847" with -- 4,051,847 --.

<u>Column 16,</u>
Line 31, replace "Operatively" with -- operatively --.

Signed and Sealed this

Fifteenth Day of April, 2003

JAMES E. ROGAN
*Director of the United States Patent and Trademark Office*